US 6,683,072 B1

(12) United States Patent
Kucharik et al.

(10) Patent No.: US 6,683,072 B1
(45) Date of Patent: Jan. 27, 2004

(54) COMPOSITIONS AND METHODS FOR TREATMENT OF IRRITABLE BOWEL SYNDROME AND NONULCER DYSPEPSIA

(75) Inventors: Robert F. Kucharik, Glenmoore, PA (US); Herbert W. Harris, Merion, PA (US)

(73) Assignee: Vela Pharmaceuticals, Inc., Lawrenceville, NJ (US)

( * ) Notice: Subject to any disclaimer, the term of this patent is extended or adjusted under 35 U.S.C. 154(b) by 0 days.

(21) Appl. No.: 10/358,034

(22) Filed: Feb. 4, 2003

(51) Int. Cl.$^7$ .............................................. A61K 31/553

(52) U.S. Cl. ................................................. 514/211.13

(58) Field of Search .................................... 514/211.13

(56) References Cited

U.S. PATENT DOCUMENTS

| | | | |
|---|---|---|---|
| 3,535,315 A | 10/1970 | Winter et al. | 549/354 |
| 3,758,528 A | 9/1973 | Malen et al. | 554/103 |
| 3,821,249 A | 6/1974 | Malen et al. | 540/549 |
| 4,459,306 A | 7/1984 | Malen et al. | 514/450 |
| 4,766,114 A | 8/1988 | Malen et al. | 514/211.13 |
| 5,888,542 A | 3/1999 | Huet de Barochez et al. | 424/464 |
| 6,441,165 B2 | 8/2002 | Blanchard et al. | 544/209 |

FOREIGN PATENT DOCUMENTS

GB 1 269 551 4/1972

OTHER PUBLICATIONS

H. Mönnikes et al., "Role of Stress in Functional Gastrointestinal Disorders", Digestive Diseases, 2001;19:201–211.

Emeran A. Mayer et al., "Basic Pathophysiologic Mechanisms in Irritable Bowel Syndrome", Digestive Diseases, 2001;19:212–218.

Brenda J. Horwitz, M.D. et al., "The Irritable Bowel Syndrome", The New England Journal of Medicine, vol. 344, No. 24—Jun. 14, 2001, pp. 1846–1850.

Emeran A. Mayer et al., "Stress and the Gastrointestinal Tract V. Stress and irritable bowel syndrome", American Journal of Physical Gastrointest Liver Physical, 280; G519–G524, 2001.

Raymond J. Bergeron et al., "Control of Irritable Bowel Syndrome with Polamine Analogs", Digestive Diseases and Sciences, vol. 46, No. 12 (Dec. 2001), pp. 2615–2623.

Howard R. Mertz, MD, et al., "New Concepts of Irritable Bowel Syndrome", Current Gastroenterology Reports 1999, 1:433–440, Current Sciences Inc. ISSN 1522–8037.

American Pharmaceutical Association, "Treatment Innovations for Irritable Bowel Syndrome", The National Professional Society of Pharmacists, Special Report: Treatment Innovations for Irritable Bowel Syndrome, 2000, pp. 1–21.

Gareth J. Sanger, "Hypersensitivity and Hyperreactivity In the Irritable Bowel Syndrome: An Opportunity for Drug Discovery", Digestive Diseases, 1999;17:90–99.

Pub Med PMID: 12150698 abstracting Jan Tack et al., "A New 5–HT4 Agonist and Colonie Propulsion", Expert Opinion on Pharmacotherapy, 2002, vol. 3, No. 8, pp. 1211–1218.

Pub Med PMID: 9243330 abstracting Nagakura Y et al., "The Selective 5–Hydroxytryptamine (5–HT)–Receptor Agonist RS67506 Enhances Lower Intestinal Propulsion in Mice", Jpn J Pharmacol, 1997, Jun;74(2):209–12.

Pub Med PMID: 10354345 abstracting Clayton NM et al., "5HT3 Antagonists and Colonic Propulsion", Neurogastroenterol Motil, 1999, Jun;11(3):207–17.

Pub Med PMID: 9200559 abstracting Nagakura Y et al., "Compounds Possessing 5–HT3 Receptor Antagonistic Activity Inhibit Intestinal Propulsion in Mice", Eur J. Pharmacol, 1996, Sep 5;311(1):67–72.

Pub Med PMID: 9862758 abstracting Jin JG et al., "Propulsion in Guinea Pig Colon Induced by 5–Hydroxytryptamine (HT) via 5–HT4 and 5–HT3 Receptors", J Pharmacol Exp Ther, 1999, Jan;288(1):93–7.

Dialog (File 144) abstracting Oluyomi A O et al., "Effects of the (+) and (−) Enantiomers of the Antidepressant Drug Tianeptine on 5–HTP–Induced Behaviour", Journal : Neuropharmacology, 1997, 36 (3) 383–387.

www.tianeptine.info/tianeptine/tianeptine–anxiety–1.htm abstracting Wilde MI et al., "Antidepressant and Anxiolytic Activities of Tianeptine: And Overview of Clinical Trials", Clin Neuropharmacol 1998;11 Suppl 2:S74–82.

www.tianeptine.info/tianeptine/tianeptine–masks–14.htm abstracting Ven, Vorob'eva, "Neurological Masks of Depression (Effectiveness of Tianeptine)", Behav Pharmacol. 2000;100(6): 21–3.

www.biopsychiatry.com/alltia.thmOct. 10, 2002 abstracting Lechin F et al., "Neuropharmacologic Treatment of Bronchial Asthma with the Antidepressant Tianeptine: A Double–Blind, Crossover Placebo–Controlled Study", Clin Pharmacol Ther 1998 Aug;64(2):223–32.

(List continued on next page.)

Primary Examiner—James H Reamer
(74) Attorney, Agent, or Firm—Drinker Biddle & Reath LLP

(57) ABSTRACT

Compounds according to the formula $$Y\text{-}\underset{\underset{R-N-(CH_2)_n-COOR'}{|}}{\overset{A}{\underset{*CH}{\bigcirc\bigcirc}}}\text{-}X$$

as defined herein are administered for the treatment of irritable bowel syndrome and nonulcer dyspepsia.

15 Claims, No Drawings

OTHER PUBLICATIONS www.biopsychiatry.cm/tianeptine.htm abstracting Wilde MI et al., "Tianeptine. A Review of its Pharmacodynamic and Pharmacokinetic Properties, and Therapeutic Efficacy in Depression and Coexisting Anxiety and Depression", *Drugs*, 1995 Mar. 49:3, 411–39.

www.biopsychiatry.com/stablon.htmOct. 10, 2002 abstracting Jaffard R R et a l, "Effect of Repeated Treatment with Tianeptine and Fluxetine on Central Dopamine D2 / D3 Receptors", *Behav Pharmacol* 2002 Mar;13(2):127–38.

www.biosychiatry.com/tianprof.htmOct. 10, 2002, abstracting to Loo H et al., "Position of Tianeptine Among Antidepressive Chemotherapies", *Clin Neuropharmacol* 1988; 11 Suppl 2:S97–102.

www.cancer.gov/cancer_information/doc abstracting Castanon N et al., "Chronic Treatment with the Atypical Antidepressant Tianeptine Attenuates Sickness Behavior Induced by Peripheal but not Central Lipopolysaccharide and Interleukin–1Beta in the Rat", Psychopharmacology (Bert); 154(1):50–60 2001 UI: 11292006.

Pub Med PMID: 10771496 abstracting Leroi AM et al., "Prolonged Stationary Colonic Motility Recording in Seven Patients with Severe Constipation Secondary to Antidepressants", Neurogastroenterol Motil 2000 Apr;12(2):149–54.

Pub Med PMID: 1630590 abstracting Invernizzi R et al., "Tianeptine Increases the Extracellular Concentrations of Dopamine in the Nucleus Accumbens by a Serotonin–Independent Mechanism", Neuropharmacology 1992 Mar;31(3):221–7.

Pub Med PMID: 11463130 abstracting Wagstaff AJ et al., "Tianeptine: A Review of its Use in Depressive Disorders", CNS Drugs 2001;15(3):231–59.

Richard B. Lynn et al., "Irritable Bowel Syndrome", The New England Journal of Medicine, Review Article, Current Concepts, vol. 329:1940–1945, Dec. 23, 1993, No. 26.

L. Bueno et al., "Inhibition of Stress–Induced Colonic Motor Alternations By Tianeptine", $9^{th}$ World of Congress of Psychiatry, Abstracts, p. 200, Abstract No. 782, Jun. $6^{th}$ –$12^{th}$ 1993—Brazil.

COMPOSITIONS AND METHODS FOR TREATMENT OF IRRITABLE BOWEL SYNDROME AND NONULCER DYSPEPSIA

FIELD OF THE INVENTION

The present invention relates to methods of treatment for irritable bowel syndrome and nonulcer dyspepsia.

BACKGROUND OF THE INVENTION

Irritable bowel syndrome (IBS) is a common functional disorder of the bowel that has a pronounced effect on quality of life. The syndrome is characterized by an altered regulation of bowel motility, chronic abdominal pain or discomfort, and changes in bowel patterns. The changes in bowel patterns can manifest as loose or more frequent bowel movements, diarrhea, and/or constipation. IBS is divided into four subcategories according to whether the predominant symptom is abdominal pain, diarrhea, constipation, or constipation alternating with diarrhea.

Approximately 15 percent of U.S. adults report symptoms that are consistent with the diagnosis of IBS. Nevertheless, it is estimated that only 25 percent of persons with IBS seek medical care. Studies suggest that those who seek care for IBS are also more likely to have accompanying behavioral and psychiatric problems than are those who do not seek care. In addition, patients diagnosed with IBS are at increased risk for other, non-gastrointestinal functional disorders such as fibromyalgia and interstitial cystitis.

IBS appears to affect three times as many women as men. Whether this difference reflects a true predominance of the disorder among women, or merely because women are more likely to seek medical care, has not been determined.

IBS is the most common diagnosis made by gastroenterologists in the U.S., and accounts for 12 percent of visits to primary care providers. Approximately $8 billion in direct medical costs and $25 billion in indirect costs are spent annually in the U.S for diagnosing and treating IBS. Thus, IBS accounts for a large proportion of annual healthcare costs in the U.S.

Converging evidence indicates that IBS results from altered regulation of gastrointestinal motility and epithelial function, as well as from an altered perception of visceral events. See Mayer et al., *Digestive Diseases,* 19:212–218, 2001. Altered bowel motility, visceral hypersensitivity, psychosocial factors, an imbalance in neurotransmitters, and infection have also been proposed as playing a part in the development of IBS. See Horwitz B et al., *New Engl J Med,* 344:24, 2001.

Current therapies for IBS include behavioral modification and training to gain increased awareness of visceral functions, dietary modifications, and treatment with antidiarrheals (e.g., loperamide), antispasmodics or anticholinergic agents. However, none of these therapies are effective for the long-term alleviation of the multiple symptoms of IBS.

Zelnorm™, a partial agonist of the 5-HT$_4$ serotonin receptor, has been approved for short-term treatment of abdominal pain, bloating and constipation in women with IBS. However, this drug has not been shown to work in men, and is not indicated for female IBS patients whose symptoms include diarrhea. Also, there are concerns about the safety of long-term use of Zelnorm™. See DeNoon D. et al., WebMD Medical News, Oct. 29, 2002.

Nonulcer dyspepsia (NUD) is another common ftmctional disorder of the bowel. NUD is defined as chronic or recurrent upper abdominal pain or discomfort for a period of more than three months' duration, in the absence of another organic cause. The NUD symptoms must be present for more than 25 percent of the time. See Fisher RS, Parkman HP, *New Engl J Med* 1998; 339: 1376–1381. NUD has also been characterized as "persistent or recurrent upper abdominal pain or discomfort with no structural or biochemical explanation for the patient's symptoms." See Locke GR, *Mayo Clin Proc* 1999;74:1011–15. Other symptoms associated with NUD include bloating, nausea, early satiety, eructation and heartburn.

NUD has many similarities to IBS. In fact, patients presenting with idiopathic gastrointestinal pain fall into a continuum of functional gastrointestinal disorders which include NUD and IBS. See Freidman LS, *New Engl J Med* 1998; 339: 1928–30. NUD and IBS are usually differentiated by determining whether the abdominal pain reported by the patient is associated with abnormal bowel habits. If such an association is present, the condition is considered to be IBS rather than NUD.

Like IBS, the cause of NUD is not well understood. NUD is most likely caused by an alteration in the perception of sensations arising from the gut. Other possible causes of NUD have been investigated, including *Helicobacter pylori* infection. However, no clear relationship has been established between curing an *H. pylori* infection and improvement of NUD. An alteration in stomach function has also been implicated in NUD. For example, about 25–50% of patients with NUD exhibit slowed emptying from the stomach, which may in part explain the increased occurrence of symptoms after meals.

Current therapies for NUD include dietary modifications, such as eating low-fat meals or smaller, more frequent meals to help reduce the symptoms experienced after eating. Other therapies include administering agents to decrease stomach acid, agents to enhance stomach emptying (prokinetic agents) or antibiotics to treat *H. pylori* infection. Antidiarrheals and antispasmodics prescribed for IBS can also be used to treat NUD. However, similar to IBS, none of these therapies significantly improves the overall symptoms in patients with NUD.

Tianeptine, which has the systematic name 7-[(3-chloro-6,11-dihydro-6-methyl-dibenzo[c,f][1,2] thiazepin-11-yl) amino] heptanoic acid S,S-dioxide, is a tricyclic antidepressant of the dibenzothiazepine type. Tianeptine is known to have psychostimulant, anti-depressive, analgesic, antitussive, antihistaminic and gastric antisecretory properties. See, e.g., U.S. Pat. No. 3,758,528 of Malen et al. Tianeptine acts as a serotonin reuptake accelerator, in that it increases the presynaptic uptake of serotonin. A sodium salt of tianeptine is currently marketed over-the-counter in Europe under the trademark Stablon®. Tianeptine is used to treat neurotic or reactive states of depression, angiodepressive states with somatic complaints such as digestive problems, angiodepressive states observed in alcoholic detoxification, and asthma. The chemical formula of tianeptine is given below:

Tianeptine

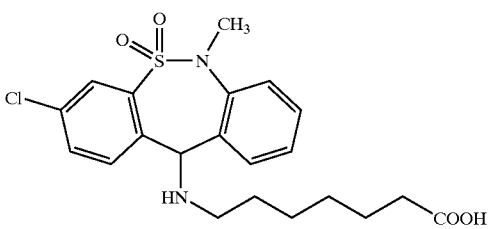

There is a need for agents which are effective in treating IBS and NUD. In particular, there is a need for agents that are appropriate for long-term use in treatment and prevention IBS and NUD, and which treat multiple symptoms or manifestations of these disorders.

SUMMARY OF THE INVENTION

Compounds of formula I can prevent or alleviate symptoms of IBS or NUD. A method of treating IBS or NUD therefore comprises administering an effective amount of at least one compound of formula I, or pharmaceutically acceptable salts thereof, to a subject in need of such treatment. Formula I is:

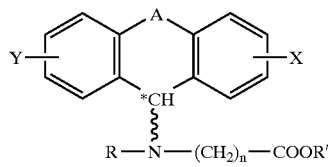

(I)

wherein:
A is a bridge selected from the following radicals:
—$CH_2)_m$—, —CH=CH—, —$(CH_2)_p$—O—, —$(CH_2)_p$—S—, —$(CH_2)_p$—$SO_2$—, —$(CH_2)_p$—$NR_1$— and —$SO_2$—$NR_2$—, and wherein:
  m is an integer of from 1 to 3 inclusive;
  p is an integer selected from 1 and 2;
  $R_1$ is selected from the group consisting of hydrogen and $C_1$–$C_5$ alkyl; and
  $R_2$ is $C_1$–$C_5$ alkyl;
X and Y are independently selected from the group consisting of hydrogen and halogen;
R and R' are independently selected from the group consisting of hydrogen and $C_1$–$C_5$ alkyl;
n is an integer from 1 to 12 inclusive, preferably 2–10 inclusive, most preferably 4–8 inclusive; and
* denotes an asymmetric carbon and the bond designated by ∿∿ indicates that the absolute conformation about the asymmetric carbon can be either (R) or (S) only when all four groups attached to the asymmetric carbon are nonequivalent.

According to one preferred embodiment, A is preferably —$SO_2$—$NR_2$—, and/or R and R' are hydrogen.

Definitions

The term "alkyl", by itself or as part of another substituent means a straight, branched or cyclic chain hydrocarbon radical, including di- and multi-radicals, having the number of carbon atoms designated (ie. $C_1$–$C_5$ means one to five carbons). Alkyl groups include straight chain, branched chain or cyclic groups, with straight being preferred. Examples include: methyl, ethyl, propyl, isopropyl, butyl, isobutyl, tert-butyl, pentyl, and neopentyl.

The term "halogen" means iodine, fluorine, chlorine and bromine atoms. Preferred halogens are fluorine, chlorine and bromine atoms.

As used herein, "optically active" refers to a property whereby a material rotates the plane of plane-polarized light. A compound that is optically active is nonsuperimposable on its mirror image. As used herein, the property of nonsuperimposability of an object on its mirror image is called "chirality." The most common structural feature producing chirality is an asymmetric carbon atom; i.e., a carbon atom having four nonequivalent groups attached thereto.

As used herein, "enantiomer" refers to each of the two nonsuperimposable isomers of a pure compound that is optically active. Single enantiomers are designated according to the Cahn-Ingold-Prelog system, which is a well-known set of priority rules for ranking the four groups attached to an asymmetric carbon. See, e.g., March, *Advanced Organic Chemistr. 4$^{th}$ Ed.*, (1992), p. 109, the entire disclosure of which is herein incorporated by reference. For example, once the priority ranking of the four groups attached to an asymmetric carbon of a molecule is determined, the molecule is oriented so that the lowest ranking group is pointed away from the viewer. If the descending rank order of the other groups proceeds clockwise, the molecule is designated (R). If the descending rank of the other groups proceeds counterclockwise, the molecule is designated (S). In the example below, the Cahn-Ingold-Prelog ranking sequence is A>B>C>D. The lowest ranking atom, D is oriented away from the viewer.

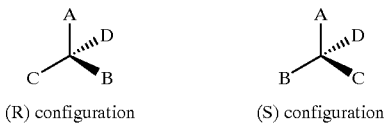

(R) configuration    (S) configuration

As used herein, "racemate" or "racemic compound" refers to a 50—50 mixture of two enantiomers such that the mixture does not rotate plane-polarized light.

By "(R)-enantiomer substantially free of the (S)-enantiomer" is meant a compound that comprises 80% or more by weight of the (R)-enantiomer, and likewise contains 20% or less by weight of the (S)-enantiomer as a contaminant. By "(S)-enantiomer substantially free of the (R)-enantiomer" is meant a compound that comprises 80% or more by weight of the (S)-enantiomer, and likewise contains 20% or less by weight of the (R)-enantiomer as a contaminant.

DETAILED DESCRIPTION OF THE INVENTION

The compounds of formula I can be readily prepared by one of ordinary skill in the art. Suitable synthetic methods are found, for example, in U.S. Pat. Nos. 4, 766,114, 3,758,528 and 3,821,249, all of Malen et al., and U.S. Pat. No. 6,441,165 of Blanchard et al., the entire disclosures of which are herein incorporated by reference.

Certain compounds of formula I, such as tianeptine (see formula II, below), possess an asymmetric carbon. The position of the asymmetric carbon is denoted by an asterisk (*) in formula I; for this carbon to be considered asymmetric, each of the four groups attached to it must be nonequivalent. One skilled in the art can readily determine which compounds of formula I possess an asymmetric carbon.

Those compounds of formula I which have this asymmetric carbon can exist as both (R) and (S) enantiomers.

Typically, the (R) and (S) enantiomers of a given compound of formula I exist as a racemate. In the practice of the present invention, both racemates and individual (R) or (S) enantiomers of a compound of formula I can be used to treat IBS or NUD. According to certain embodiments of the invention, an (R)-enantiomer of a compound of formula I which is substantially free of the corresponding (S)-enantiomer, or an (S)-enantiomer of a compound of formula I which is substantially free of the corresponding (R)-enantiomer, is used to treat IBS or NUD.

To isolate the individual (R)- and (S)-enantiomers of a compound of formula I, the racemate of that compound must be resolved. This resolution can be achieved by converting a racemic compound of formula I into a pair of diastereomers, for example by covalently bonding to an optically active moiety or by salt formation with an optically active base or acid. Either method provides a molecule with a second chiral center, thus generating a pair of diastereomers. The diastereomeric pair can then be separated by conventional methods, such as crystallization or chromatography.

For example, racemic compounds of formula I can be converted to the (S)-dibenzoyltartaric acid salt, which is a diastereomeric mixture of SS and RS configurations. The pairs of diastereomers (R,S) and (S,S) possess different properties (e.g., differential solubilities) that allow for the use of conventional separation methods. Fractional crystallization of diastereomeric salts from a suitable solvent is one such separation method.

Racemic compounds of formula I can be separated into enantiomers without diastereomer formation, for example, by differential absorption on a chiral stationary phase of a chromatography (e.g., HPLC) column. Preparative HPLC columns suitable for diastereomer separation are commercially available with a variety of packing materials to suit a broad range of separation applications. Stationary phases suitable for resolving racemic compounds of formula I include:

(i) macrocyclic glycopeptides, such as silica-bonded vancomycin which contains 18 chiral centers surrounding three pockets or cavities;

(ii) chiral $\alpha_1$-acid glycoprotein;

(iii) human serum albumin; and (iv) cellobiohydrolase (CBH).

Chiral $\alpha_1$-acid glycoprotein is a highly stable protein immobilized onto spherical silica particles that tolerates high concentrations of organic solvents, high and low pH, and high temperatures. Human serum albumin is especially suited for the resolution of weak and strong acids and zwitterionic and nonprotolytic compounds, but is also used to resolve basic compounds. CBH is a very stable enzyme that that is typically immobilized onto spherical silica particles for separating enantiomers of basic drugs from many compound classes.

Other chromatographic techniques suitable for resolving racemic compounds of formula I include chiral chromatography using macrocyclic glycopeptide as a stationary phase on a Chirobiotic V™ column (ASTEAC, Whippany, N.J.) as described in U.S. Pat. No. 6,080,736, the entire disclosure of which is herein incorporated by reference, and chiral chromatography using a chiral $\alpha_1$-acid glycoprotein as a stationary phase on a CHIRAL-AGP™ column (ChromTech, Cheshire, UK), as described in Fitos et al., *J Chromatogr.*, 1995, 709:265, the entire disclosure of which is herein incorporated by reference.

A preferred compound of formula I for use in the present methods is tianeptine, or a pharmaceutically acceptable salt thereof. The structure of tianeptine is given in formula II:

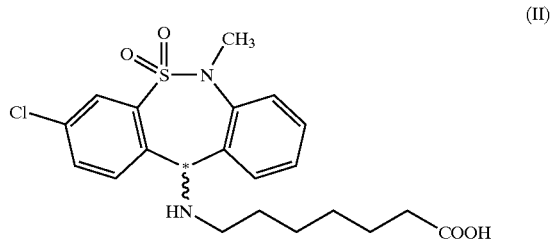

(II)

wherein:
* denotes an asymmetric carbon; and
the bond designated by ∿ indicates that the absolute conformation about the asymmetric carbon can be either (R) or (S).

Tianeptine can be readily obtained by one of ordinary skill in the art, for example by the synthetic techniques described above. Tianeptine is also sold commercially as Stablon®.

The (R) or (S) enantiomers of tianeptine can be isolated, for example, by the techniques discussed above. Thus, in preferred embodiments of the present invention, the (R)-enantiomer of tianeptine which is substantially free of the corresponding (S)-enantiomer, or the (S)-enantiomer of tianeptine which is substantially free of the corresponding (R)-enantiomer, is used in the present methods.

In the practice of the invention, the compounds of formula I described above can take the form of a pharmaceutically-acceptable salt. The term "salts", embraces salts commonly used to form alkali metal salts and to form addition salts of free acids or free bases.

For example, pharmaceutically-acceptable acid addition salts may be prepared from an inorganic acid or from an organic acid. Suitable inorganic acids include hydrochloric, hydrobromic, hydroiodic, nitric, carbonic, sulfuric and phosphoric acid. Suitable organic acids include aliphatic, cycloaliphatic, aromatic, aralphatic, heterocyclic, carboxylic and sulfonic classes of organic acids, such as formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, galactaric and galacturonic acid.

Suitable pharmaceutically acceptable base addition salts of the compounds of formula I, include metallic salts made from calcium, magnesium, potassium, sodium and zinc, or organic salts made from N,N'-dibenzylethylenediamine, chloroprocaine, choline, diethanolamine, ethylenediamine, meglumine (N-methylglucamine) and procaine. All of these salts can be prepared by conventional means from the corresponding compound of formula I by reacting, for example, the appropriate acid or base with the compound of formula I.

The compounds of formula I, in particular tianeptine, can be used to treat IBS or NUD in a subject who has been diagnosed with either disorder. As used herein, a "subject" is includes humans and non-human mammals. Non-human mammals include bovines, ovines, porcines, equines, canines, felines, and rodents (e.g., rat, mouse, guinea pig and rabbit). Preferably, the subject is a human.

Diagnosis of IBS is within the skill in the art. For example, IBS can be diagnosed on the basis of the modified "Rome criteria." The modified Rome criteria are (A) the presence for at least 12 weeks (not necessarily consecutive) in the preceding 12 months of abdominal discomfort or pain that cannot be explained by structural or biochemical abnormalities; and (B) at least two of the following three symptoms: (I) pain relieved with defecation; (2) pain, when the onset thereof is associated with a change in the frequency of bowel movements (diarrhea or constipation); and pain when the onset thereof is associated with a change in the form of the stool (lose, watery, or pellet-like).

The diagnosis of NUD is also within the skill in the art. For example, criteria for diagnosing NUD include the presence of chronic or recurrent upper abdominal pain or discomfort for a period of more than three months' duration, which has no apparent organic cause. These symptoms must be present for more than 25 percent of the time. Bloating, nausea, early satiety, eructation and heartburn may also be present. See, e.g., Fisher RS, Parkman HP, *New Engl J Med* 1998; 339: 1376–1381 and Locke GR, *Mayo Clin Proc* 1999;74:1011–15, the entire disclosures of which are herein incorporated by reference. NUD can be differentiated from IBS by determining whether the abdominal pain reported by the subject is associated with abnormal bowel habits. If such an association is present, the condition is considered to be IBS rather than NUD. See Freidman LS, *New Engl J Med* 1998; 339: 1928–30, the entire disclosure of which is herein incorporated by reference.

In the practice of the invention, IBS or NUD are treated by administering an effective amount of at least one compound of formula I to a subject in need of such treatment, such that the symptoms of IBS or NUD are reduced.

As used herein, an "effective amount" of a compound of formula I used to treat IBS refers to the amount of the compound that prevents or alleviates one or more symptoms of IBS. A physician can readily determine when symptoms of IBS are prevented or alleviated, for example through clinical observation of a subject, or through reporting of symptoms by the subject during the course of treatment. Likewise, an "effective amount" of a compound of formula I used to treat NUD refers to the amount of the compound that prevents or alleviates the symptoms of NUD. Again, a physician can readily determine when symptoms of NUD are prevented or alleviated through clinical observation of a subject or through reporting of symptoms by the subject during the course of treatment.

One skilled in the art can readily determine an effective amount of a compound of formula I to be administered, by taking into account factors such as the size, weight, age and sex of the subject, the extent of disease penetration or persistence and severity of symptoms, and the route of administration. Generally, an effective amount of the compounds of formula I administered to a subject is from about 2 to about 100 mg/kg/day, preferably from about 5 to about 60 mg/kg/day, and more preferably about 30 mg/kg/day. Higher or lower doses are also contemplated.

The compounds of formula I can be administered to a subject by any route, for example by enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of the compounds of formula I into the body of the subject, for example in a controlled release formulation, with systemic or local release of the compound to occur over time or at a later time. Preferably, the compound of formula I is localized in a depot for controlled release to the circulation or to a local site such as the gastrointestinal tract.

In the practice of the present methods, compounds of formula I can be administered in the form of a pharmaceutical composition comprising at least one compound of formula I and a pharmaceutically acceptable carrier. Pharmaceutical formulations of the invention can comprise from 0.1 to 99.99 weight percent of at least one compound of formula I. The pharmaceutical compositions of the invention can be formulated according to standard practices in the field of pharmaceutical preparations. See Alphonso Gennaro, ed., *Remington's Pharmaceutical Sciences.* 18th Ed., (1990) Mack Publishing Co., Easton, Pa. Suitable dosage forms can comprise, for example, tablets, capsules, solutions, parenteral solutions, troches, suppositories, or suspensions.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices.

Pharmaceutical compositions of the invention for parenteral administration can take the form of an aqueous or nonaqueous solution, dispersion, suspension or emulsion. In preparing pharmaceutical compositions of the invention for parenteral administration, at least one compound of formula I can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of at least one compound of formula I. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propylparaben, and chlorbutanol.

In preparing pharmaceutical compositions of the invention for oral administration, at least one compound of formula I can be combined with one or more solid or liquid inactive ingredients to form tablets, capsules, pills, powders, granules or other suitable oral dosage forms. For example, at least one compound of formula I can be combined with at least one pharmaceutically acceptable carrier such as a solvent, filler, binder, humectant, disintegrating agent, solution retarder, absorption accelerator, wetting agent absorbent or lubricating agent. In one embodiment, at least one compound of formula I is combined with carboxymethylcellulose calcium, magnesium stearate, mannitol and starch, and is formed into tablets by conventional tableting methods. In a preferred embodiment, tianeptine is formulated into a tablet comprising cellulose and a calcium salt, as described in U.S. Pat. No. 5,888,542, the entire disclosure of which is herein incorporated by reference.

Pharmaceutical compositions of the invention can also be formulated so as to provide controlled-release of at least one compound of formula I upon administration of the composition to a subject. Preferably, a controlled-release pharmaceutical composition of the invention is capable of releasing at least one compound of formula I into a subject at a desired rate, so as to maintain a substantially constant pharmacological activity for a given period of time.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,059,595 (gastro-resistant tablet), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise at least one compound of formula I and a controlled-release component. As used herein, a "controlled-release component" is a compound such as a polymer, polymer matrix, gel, permeable membrane, liposome and/or microsphere that induces the controlled-release of the compound of formula I into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, at least one compound of formula I is incorporated into a sol-gel matrix that is a solid at room temperature. This sol-gel matrix is implanted into a subject having a body temperature high enough to induce gel formation of the sol-gel matrix, thereby releasing the active ingredient into the subject.

The practice of the invention is illustrated by the following non-limiting example.

EXAMPLE 1

Colonic Propulsion Study in the Mouse

The model used in the present study is predictive of agents that can be used to treat the alterations in propulsion of intestinal contents that occur in IBS. The model is sensitive to test compounds which produce inhibitory effects on propulsive motor activity, but is not sensitive to test compounds which increase colonic propulsive motility. The model thus provides a direct measure of colonic propulsion by measuring movement of a glass bead through the mouse colon. Test compounds that slow the rate at which the glass bead is expelled are predicted to have utility in the treatment of IBS.

The model used in the present study can also evaluate test compounds that may cause constipation, have antidiarrheal activity, or have selective visceral anti-nociceptive activity. Thus, the model is useful for evaluating test compounds for treating NUD as well as IBS.

For the present study, 48 female, 6 week old Swiss Webster mice (18–30 g) were divided into the following test groups: three treatment groups receiving, respectively, 10 mg/kg tianeptine (n=9), 30 mg/kg tianeptine (n=10), and 60 mg/kg tianeptine (n=9); a control group receiving 10 mg/kg of the antidiarrheal loperamide (n=9); and a control group receiving vehicle only (n=10). Each animal was dosed orally with either tianeptine, loperamide or vehicle, as appropriate.

Thirty minutes after dosing, a 3 mm glass bead was inserted through the anus of each animal into the distal colon to a depth of 2 cm, using a glass rod. The animals were observed for expulsion of the bead, and the time of expulsion was noted. Any animal that had not expelled the bead within a cut-off time of 60 minutes after bead insertion was sacrificed, and the position of the bead in the lumen of the colon was verified. Mean and standard error of the mean were calculated for the expulsion times for each group. The data are summarized in Table 1 below.

The animals were also observed for signs of gross toxicity and/or behavioral changes during the 60–90 minute interval after dosing. Such observations included gross evaluation of skin and fur, eyes and mucous membranes, respiratory, circulatory, autonomic and central nervous system, somatomotor activity and behavioral patterns. Particular attention was directed to observation of tremors, convulsions, salivation, diarrhea, sleep and coma No signs of gross toxicity or behavioral changes were observed.

TABLE 1

The Glass Bead Test of Colonic Propulsive Motility in Mice.

| Test Compound | n | Dose mg/kg PO | Expulsion Time (min.) Mean ± SEM | % Inhibition |
|---|---|---|---|---|
| vehicle | 10 | — | 8.5 ± 0.8 | — |
| loperamide | 9 | 10 | 26.0 ± 2.6* | 81 |
| tianeptine | 9 | 10 | 16.6 ± 3.6* | 38 |
| tianeptine | 10 | 30 | 25.7 ± 2.3* | 80 |
| tianeptine | 10 | 60 | 29.8 ± 0.2* | 98 |

*Statistically significant from vehicle control, $p < 0.05$ by one-way ANOVA and Dunnett Multiple Comparison Test These data show that tianeptine produces a dose-related inhibition of colonic propulsion. The 30 mg/kg tianeptine dose was equivalent in effect to a 10 mg/kg dose of loperamide. Thus, compounds of formula I, in particular tianeptine, are useful in the treatment of IBS and NUD.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating irritable bowel syndrome or nonulcer dyspepsia in a subject in need of such treatment, comprising administering to the subject an effective amount of at least one compound of formula I

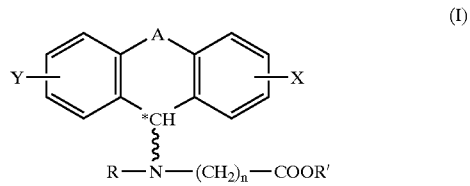

wherein:
  A is a bridge selected from the following radicals: —$(CH_2)_m$—, —CH=CH—, —$(CH_2)_p$—O—, —$(CH_2)_p$—S—, —$(CH_2)_p$—$SO_2$—, —$(CH_2)_p$—$NR_1$— and —$SO_2$—$NR_2$—, and wherein:
  m is an integer of from 1 to 3 inclusive;
  p is an integer selected from 1 and 2;
  $R_1$ is selected from the group consisting of hydrogen and $C_1$–$C_5$ alkyl; and
  $R_2$ is $C_1$–$C_5$ alkyl;
  X and Y are independently selected from the group consisting of hydrogen and halogen;

R and R' are independently selected from the group consisting of hydrogen and $C_1$–$C_5$ alkyl;

n is an integer from 1 to 12 inclusive; and

\* denotes an asymmetric carbon and the bond designated by ∿∿ indicates that the absolute conformation about the asymmetric carbon can be either (R) or (S) only when all four groups attached to the asymmetric carbon are nonequivalent, or a pharmaceutically acceptable salt thereof.

2. The method according to claim 1, wherein A is —$SO_2$—$NR_2$—.

3. The method according to claim 2, wherein R and R' are hydrogen.

4. The method of claim 3, wherein the compound of formula I is tianeptine or a pharmaceutically acceptable salt thereof.

5. The method of claim 4, wherein the compound is (R)-tianeptine, substantially free of the corresponding (S)-enantiomer.

6. The method of claim 4, wherein the compound is (S)-tianeptine, substantially free of the corresponding (R)-enantiomer.

7. The method of claim 1, wherein the subject is a human.

8. The method of claim 1, wherein the effective amount of the at least one compound of formula I administered to the subject is from about 2 to about 100 mg/kg/day.

9. The method of claim 1, wherein the effective amount of the at least one compound of formula I administered to the subject is from about 5 to about 60 mg/kg/day.

10. The method of claim 1, wherein the effective amount of the at least one compound of formula I administered to the subject is about 30 mg/kg/day.

11. The method of claim 1, wherein the at least one compound of formula I is administered by an enteral administration route.

12. The method of claim 1, wherein the at least one compound of formula I is administered by a parenteral administration route.

13. The method of claim 1, wherein the parenteral administration route is selected from the group consisting of intravenous, intramuscular, intraarterial, intraperitoneal, intravaginal, intravesical, intradermal, topical, subcutaneous, and instillation into the body of the subject.

14. The method of claim 1, wherein the at least one compound of formula I is administered to the subject as a pharmaceutical composition.

15. The method of claim 14, wherein the pharmaceutical composition comprises a controlled-release pharmaceutical composition.

\* \* \* \* \*

UNITED STATES PATENT AND TRADEMARK OFFICE
CERTIFICATE OF CORRECTION

PATENT NO. : 6,683,072 B1
DATED : January 27, 2004
INVENTOR(S) : Robert F. Kucharik et al.

It is certified that error appears in the above-identified patent and that said Letters Patent is hereby corrected as shown below:

Column 7,
Line 55, change "mg/kg/day" to -- mg/day --.
Line 56, change both occurrences of "mg/kg/day" to -- mg/day --.

Column 11,
Line 26, change "mg/kg/day" to -- mg/day --.

Column 12,
Lines 3 and 6, change "mg/kg/day" to -- mg/day --.

Signed and Sealed this

Fourth Day of January, 2005

JON W. DUDAS
*Director of the United States Patent and Trademark Office*